US00PP09578P

United States Patent [19]

Fuess

[11] Patent Number: Plant 9,578

[45] Date of Patent: Jun. 11, 1996

[54] CHRYSANTHEMUM PLANT NAMED 'EMPIRE SALSA'

[75] Inventor: Janet S. Fuess, New York Mills, N.Y.

[73] Assignee: Yoder Brothers Inc., Barberton, Ohio

[21] Appl. No.: 519,355

[22] Filed: Aug. 25, 1995

[51] Int. Cl.[6] ..... A01H 5/00

[52] U.S. Cl. ..... Plt./74.1

[58] Field of Search ..... Plt./74.1, 82.5

[56] References Cited

U.S. PATENT DOCUMENTS

P.P. 5,660 2/1986 Duffett ..... Plt./74.1

P.P. 5,695 3/1986 Tremaine et al. ..... Plt./74.1

*Primary Examiner*—Howard J. Locker

*Attorney, Agent, or Firm*—Foley & Lardner

[57] ABSTRACT

A Chrysanthemum plant named Empire Salsa particularly characterized by its flat capitulum form; daisy capitulum type; red-purple ray floret color; diameter across face of capitulum of 60 to 64 mm when fully opened; spreading branching pattern; natural season flower date of August 22 to 23 when planting rooted cuttings on June 17 to 18 in Salinas, Calif., and September 15 to 22 when planting rooted cuttings June 15 to 22 in Hightstown, N.J.; plant height of 23 to 28 cm when grown in fall under natural daylength with no growth regulators; and durable, uniform performance.

3 Drawing Sheets

The present invention comprises a new and distinct cultivar of Chrysanthemum, botanically known as *Dendranthema grandiflora,* and referred to by the cultivar name Empire Salsa.

Empire Salsa, identified as 9852 (Z91-2), was originated from a cross made by the inventor the inventor Janet S. Fuess in a controlled breeding program in New Hartford, N.Y. in October 1990.

The female parent of Empire Salsa was an unnamed seedling, identified as D90-16, and described as a bronze daisy garden mum.

The male parent of Empire Salsa was an unnamed seedling, identified as C90-3, and described as a red daisy garden mum.

Empire Salsa was discovered and selected as one flowering plant within the progeny of the stated cross by Janet S. Fuess in September 1991 in New Hartford, N.Y.

The first act of asexual reproduction of Empire Salsa was accomplished when vegetative cuttings were taken from the initial selection in October 1991 in a controlled environment in New Hartford, N.Y. by Janet s. Fuess.

Horticultural examination of controlled flowerings of successive plantings has shown that the unique combination of characteristics as herein disclosed for Empire Salsa are firmly fixed and are retained through successive generations of asexual reproduction.

Empire Salsa has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Empire Salsa, which, in combination, distinguish this Chrysanthemum as a new and distinct cultivar:

1. Flat capitulum form.
2. Daisy capitulum type.
3. Red-purple ray floret color.
4. Diameter across face of capitulum of 60 to 64 mm when fully opened.

5. Branching pattern is spreading.
6. Natural season flower date of August 22 to 23 when planting rooted cuttings on June 17 and 18 in Salinas, Calif., and of September 15 to 22 when planting rooted cuttings June 15 to 22 in Hightstown, N.J.
7. Plant height of 23 to 28 cm when grown in fall under natural daylength with no growth regulators.
8. Durable, uniform performance.

The accompanying photographic drawings show typical inflorescence and leaf characteristics of Empire Salsa, with the colors being as nearly true as possible with illustrations of this type.

Sheet 1 is a color photograph of Empire Salsa grown in natural season outside conditions in Salinas, Calif.

Sheet 2 is a black and white photograph of three views of the inflorescence of Empire Salsa.

Sheet 3 is a black and white photograph showing the upper and under sides of the leaves of Empire Salsa at 3 stages of development (mature, intermediate and immature). In sheets 2 and 3 a measuring tape in centimeters has been added.

Of the commercial cultivars known to the inventor, the most similar in comparison to Empire Salsa is the cultivar identified as Sandy, disclosed in U.S. Plant Pat. No. 7,531. Reference is made to attached Chart A, which compares certain characteristics of Empire Salsa to the same characteristics of Sandy.

Similar traits are capitulum form and type, and branching pattern. The ray floret color of Empire Salsa is red-purple (RHS 60A to 60B), while the ray floret color of Sandy is described as honey-bronzed (R.H.S. 13C, very slightly tinged with 24B). Empire Salsa has a smaller diameter of capitulum, an earlier natural season flower date, and a shorter plant height when compared with Sandy.

In the following description color references are made to The Royal Horticultural Society Colour Chart. The color values were determined on plant material grown as a pinched garden mum grown outdoors in Salinas, Calif. on Aug. 22, 1994.

Classification:

*Botanical.*—*Dendranthema grandiflora* cv Empire Salsa.

*Commercial.*—Flat daisy garden mum.

INFLORESCENCE

A. Capitulum:
*Form.*—Flat
*Type.*—Daisy
*Diameter across face.*—60 to 64 mm when fully opened.

B. Corolla of ray florets:
*Color (general tonality from a distance of three meters).*—Red-purple.
*Color (upper surface).*—60A to 60B.
*Color (under surface).*—182D, overlaid with 60B.
*Shape.*—Flat, straight.

C. Corolla of disc florets:
*Color (mature).*—15B.
*Color (immature).*—6B.

D. Reproductive organs:
*Androecium.*—Present on disc florets only; moderate pollen.
*Gynoecium.*—Present on both ray and disc florets.

PLANT

A. General appearance:
*Height.*—23 to 28 cm when grown in fall under natural daylength with no growth regulators.
*Branching pattern.*—Spreading.

B. Foliage:
*Color (upper surface).*—147A.
*Color (under surface).*—147B.
*Shape.*—Deeply lobed, slightly serrated.

CHART A

| Characteristic | Empire Salsa | Sandy |
|---|---|---|
| Ray floret color | Red-purple | Honey-bronze |
| Capitulum form and type | Flat<br>Daisy | Flat<br>Daisy |
| Diameter across fac of capitulum | 60 to 64 mm | 63 to 73 mm |
| Branching pattern | Spreading | Spreading |
| Natural season flower date: | | |
| in Salinas, CA | Aug 22 to 23 | Aug 25 to 28 |
| in Hightstown, NJ | Sep 15 to 22 | Sep 23 to 28 |
| Plant height: | 23 to 28 cm | 30 to 35 cm |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

I claim:

1. A new and distinct Chrysanthemum plant named Empire Salsa, as described and illustrated.

* * * * *

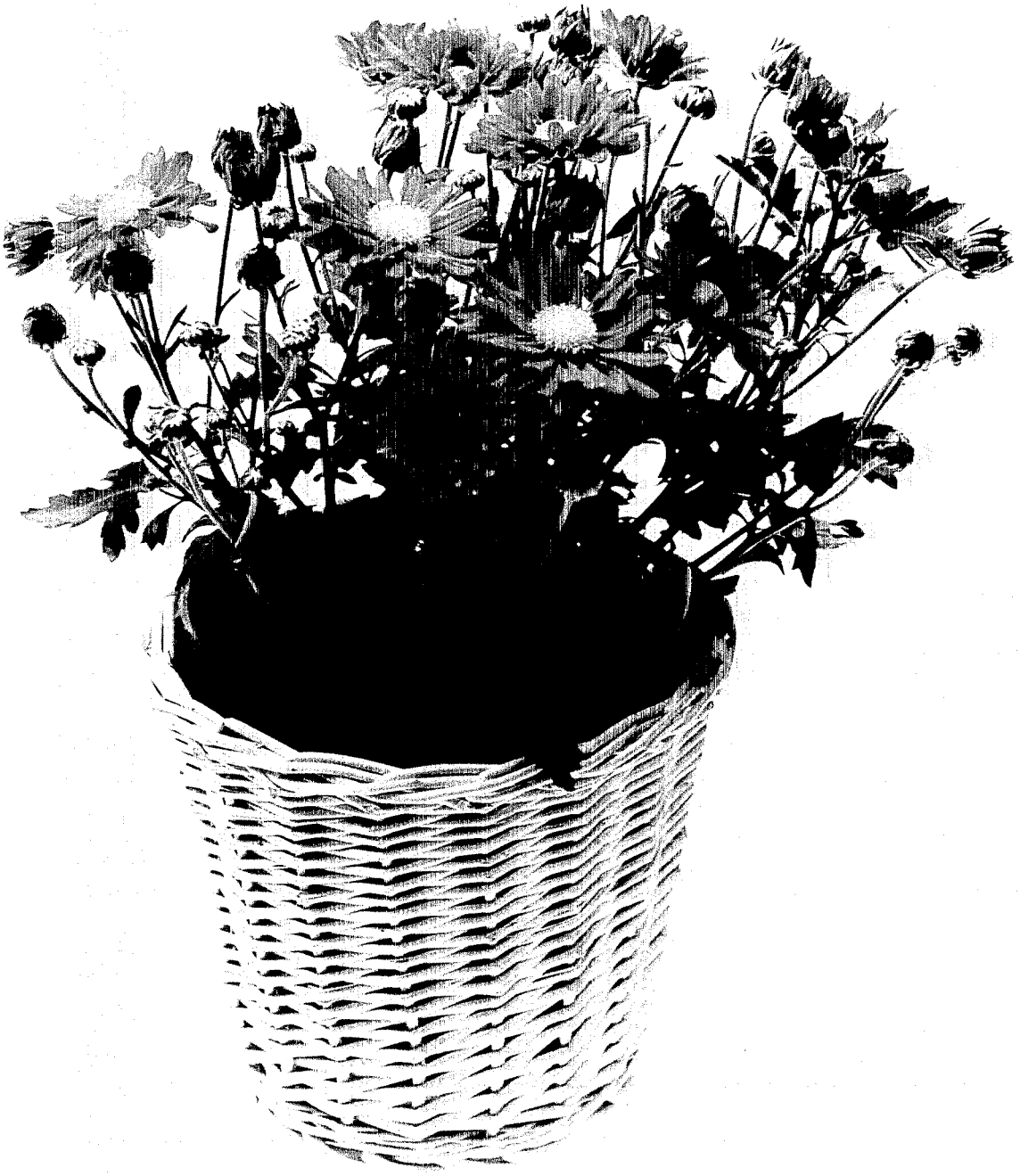

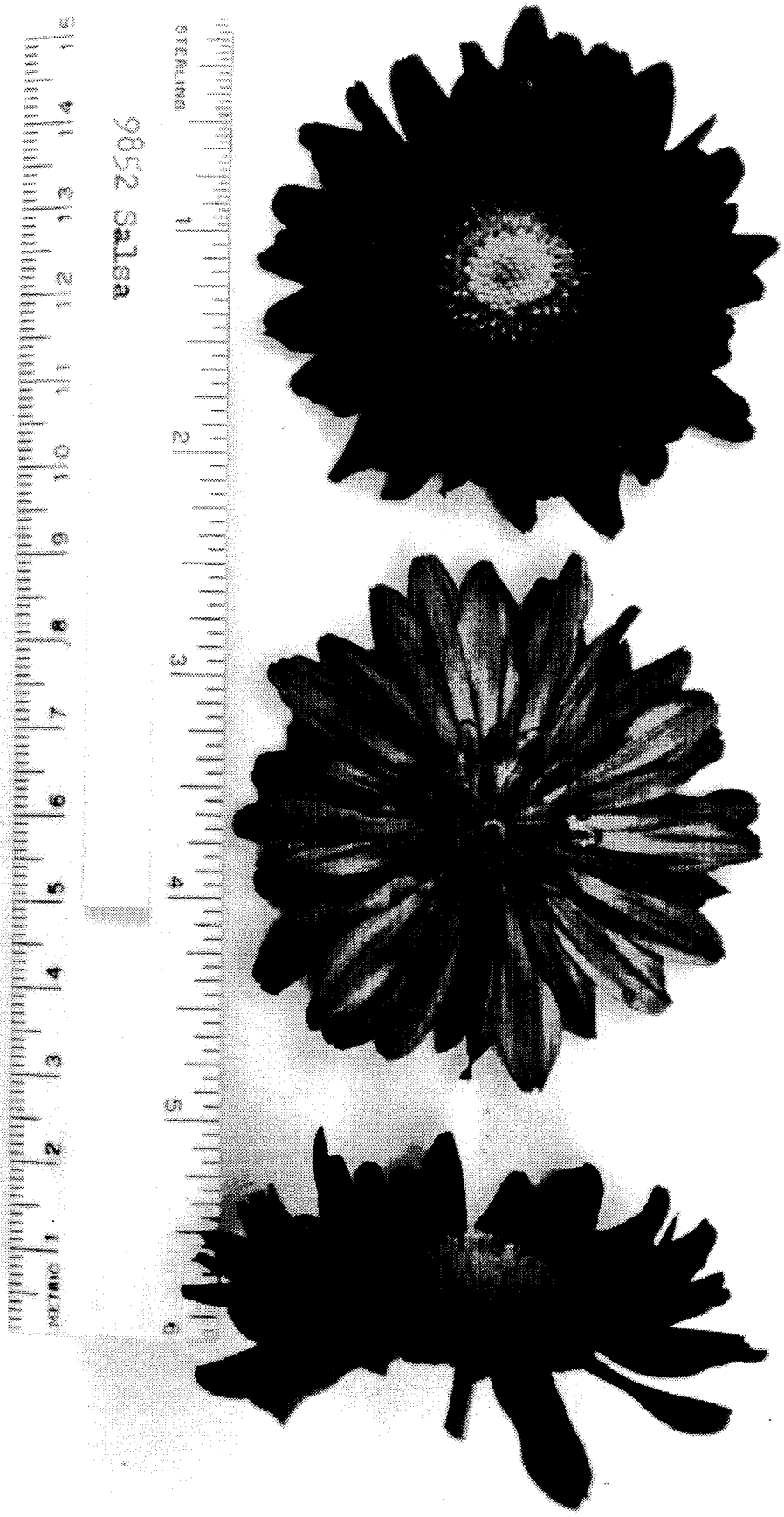
9852 Salsa

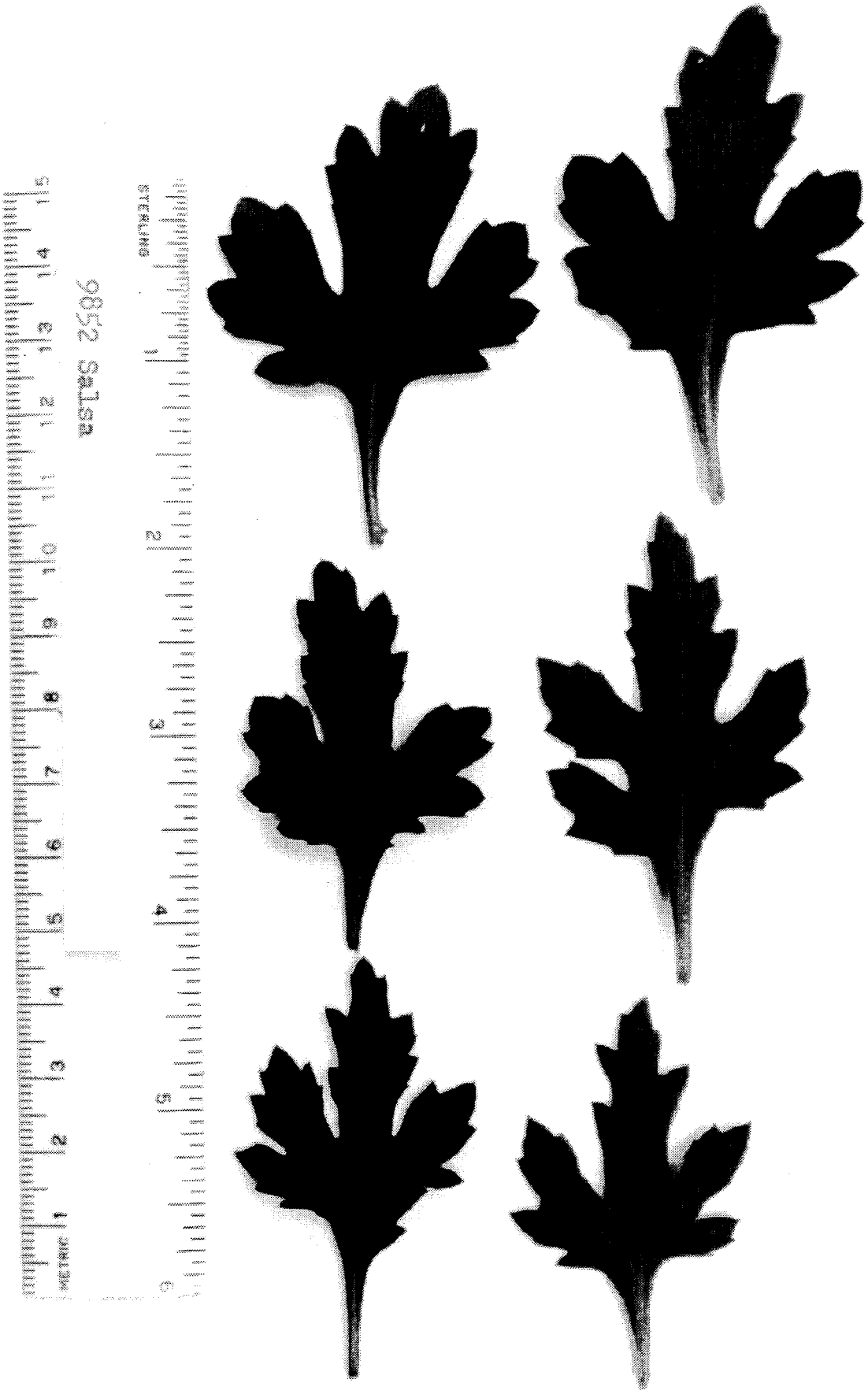
9852 Salsa